(12) United States Patent
Bond et al.

(10) Patent No.: US 7,943,139 B2
(45) Date of Patent: *May 17, 2011

(54) METHODS OF GENERATING A HUMORAL IMMUNE RESPONSE AGAINST HUMAN IMMUNODEFICIENCY VIRUS (HIV) COMPRISING ADMINISTERING NEF APOPTOTIC MOTIF-CONTAINING POLYPEPTIDE-CONJUGATES

(75) Inventors: Vincent C. Bond, Stone Mountain, GA (US); Michael Powel, Douglasville, GA (US); Ming Bo Huang, Atlanta, GA (US); Cleve James, Washington, DC (US)

(73) Assignee: Morehouse School of Medicine, Atlanta, GA (US)

( * ) Notice: Subject to any disclaimer, the term of this patent is extended or adjusted under 35 U.S.C. 154(b) by 662 days.

This patent is subject to a terminal disclaimer.

(21) Appl. No.: 11/030,315

(22) Filed: Jan. 7, 2005

(65) Prior Publication Data

US 2005/0180984 A1 Aug. 18, 2005

Related U.S. Application Data

(60) Provisional application No. 60/534,963, filed on Jan. 9, 2004.

(51) Int. Cl.
*A61K 39/21* (2006.01)
*A61K 39/385* (2006.01)

(52) U.S. Cl. .............. 424/188.1; 424/208.1; 424/196.11

(58) Field of Classification Search ........................ None
See application file for complete search history.

(56) References Cited

U.S. PATENT DOCUMENTS

| | | | |
|---|---|---|---|
| 5,705,612 A | 1/1998 | Alizon et al. | |
| 6,020,171 A | 2/2000 | Saito et al. | |
| 7,312,305 B2 * | 12/2007 | Bond et al. | 530/328 |
| 2001/0008627 A1 | 7/2001 | Soll et al. | |
| 2003/0158134 A1 | 8/2003 | Voss | |

OTHER PUBLICATIONS

Burton, D. R., and J. P. Moore, 1998, "Why do we not have an HIV vaccine and how can we make one?", Nat. Med. Vacc. Suppl. 4(5):495-498.*
Moore, J. P., and D. R. Burton, 1999, "HIV-1 neutralizing antibodies: How full is the bottle?", Nat. Med. 5(2):142-144.*
Nabel, G. J., 2001, "Challenges and opportunities for development of an AIDS vaccine", Nature 410:1002-1007.*
Feinberg, M. B., and J. P. Moore, 2002, "AIDS vaccine models: Challenging challenge viruses", Nat. Med. 8(3):207-210.*
McMichael, A. J., and T. Hanke, 2003, "HIV vaccines 1983-2003", Nat. Med. 9(7):874-880.*
Altman, J. D., and M. B. Feinberg, 2004, "HIV escape: there and back again", Nat. Med. 10(3):229-230.*
Desrosiers, R. C., 2004, "Prospects for an AIDS vaccine", Nat. Med. 10(3):221-223.*
Pantaleo, G., and R. A. Koup, 2004, "Correlates of immune protection in HIV-1 infection: what we know, what we don't know, what we should know", Nat. Med. 10(8):806-810.*
Alimonti, J. B., et al., 2003, Mechanisms of CD4+ T lymphocyte cell death in human immunodeficiency virus infection and AIDS, J. Gen. Virol. 84:1649-1661.*
Lenardo, M. J., et al., 2002, Cytopathic killing of peripheral blood CD4+ T lymphocytes by human immunodeficiency virus type 1 appears necrotic rather than apoptotic and does not require env, J. Virol. 76(10):5082-5093.*
Herbeuval, J.-P., and G. M. Shearer, 2007, HIV-1 immunopathogenesis: How good interferon turns bad, Clin. Immunol. 123:121-128.*
Huang, J., et al. 2002. A predefined epitope-specific monoclonal antibody recognizes ELDEWA-epitope just presenting on gp41 of HIV-1 O clade. Immunol. Letters 84(3):205-209.*
International Search Report, International Preliminary Report on Patentability and the Written Opinion of the International Search Authority for PCT/US2005/070041.

* cited by examiner

*Primary Examiner* — Jeffrey Parkin
(74) *Attorney, Agent, or Firm* — Ping Wang; Andrews Kurth LLP

(57) ABSTRACT

A small peptide of 10 or 11 mers, when linked to an immunogenic moiety, can protect against naferious effects of Nef protein of HIV. The vaccine is not used to induce sterilizing immunity, but to block the ability of soluble Nef protein to induce apoptosis, and to therefore alleviate lymphocyte depletion and organ damage.

10 Claims, No Drawings

SEQUENCE LISTING

```
<160> NUMBER OF SEQ ID NOS: 21

<210> SEQ ID NO 1
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1 gggggaagc ctcatatggg tggcaagtgg tcaaaaagta gtgt                    44

<210> SEQ ID NO 2
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggagggctgc agtcagtgat ggtgatggtg atgtccgccg gatccaccgc agttcttgaa    60
gtactccgg                                                           69

<210> SEQ ID NO 3
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cctagaagaa taagacaggg c                                             21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcagttcttg aagtactccg g                                             21

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aatacagcag ctaacgagga ggaagaggtg                                    30

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cacctcttcc tcctcgttag cagctgctgt att                                33

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cctagaagaa taagacaggg c                                             21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gcagttcttg aagtactccg g                                             21

<210> SEQ ID NO 9
<211> LENGTH: 30
<212> TYPE: DNA
```

-continued

<213> ORGANISM: Artificial Sequence
<220> FEATURE:
<223> OTHER INFORMATION: Description of Artificial Sequence: Synthetic
      primer

<400> SEQUENCE: 9
cctgtgagcc tgcatgagtg gaggtttgac                                           30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gtcaaacctc cactcatgca ggctcacagg                                           30

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cctagaagaa taagacaggg c                                                    21

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cactacttga agcactcaag gc                                                   22

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cctcttcagc taccaccgct tgagagactt actc                                      34

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tgactaaaat ggtctgagg                                                       19

<210> SEQ ID NO 15
<211> LENGTH: 22
<212> TYPE: DNA
<213> ORGANISM: Artificial Sequence
<220> FEATURE:

-continued

<223> OTHER INFORMATION: Description of Artificial Sequence: Synthetic
      primer

<400> SEQUENCE: 15
gaagaaggag gtggaaacga cg                                             22

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aagtgctggt gagagtctag c                                              21

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asn Ala Ala Cys Ala Trp Leu Glu Ala Gln
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Leu Ala Glu Thr Cys Gln Asn Ala Trp Ala
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Thr Asn Ala Ala Cys Ala Trp Leu Glu Ala Gln
1               5                   10

<210> SEQ ID NO 20
<211> LENGTH: 20
<212> TYPE: PRT
<213> ORGANISM: Human immunodeficiency virus type 2

<400> SEQUENCE: 20

Ser Gly Leu Pro Glu Lys Glu Trp Lys Ala Arg Leu Lys Ala Arg Gly
1               5                   10                  15

Ile Pro Thr Glu
            20

<210> SEQ ID NO 21
<211> LENGTH: 27
<212> TYPE: PRT

-continued

```
<213> ORGANISM: Simian immunodeficiency virus

<400> SEQUENCE: 21

Ser Gly Leu Ser Glu Glu Glu Val Arg Arg Arg Leu Thr Ala Arg Gly
  1               5                  10                  15

Leu Leu Asn Met Ala Asp Lys Lys Glu Thr Arg
             20                  25
```

METHODS OF GENERATING A HUMORAL IMMUNE RESPONSE AGAINST HUMAN IMMUNODEFICIENCY VIRUS (HIV) COMPRISING ADMINISTERING NEF APOPTOTIC MOTIF-CONTAINING POLYPEPTIDE-CONJUGATES

This application takes priority from Provisional Application 60/534,963 filed Jan. 9, 2004.

FIELD OF THE INVENTION

This invention relates to the use of specific Human Immunodeficiency Virus Type 1 (HIV-1) Nef peptide sequences as therapeutic agents against HIV-1-induced pathogenesis leading to AIDS. The useful peptides are referred to herein as modulators.

BACKGROUND OF THE INVENTION

Despite recent advances in research to develop a vaccine to slow or stop the progression of HIV-1 infection to AIDS, a fully or even partially efficacious vaccine remains elusive. There is a body of literature that provides circumstantial evidence suggesting that the Nef protein is a major determinant of HIV and SIV pathogenesis. Primates and humans infected with nef-deleted viral strains have delayed, or no pathogenicity. Mice and rats expressing nef as a transgene develop symptoms similar to those observed in human AIDS patients. Nef protein has been linked with the induction of apoptosis. Our preliminary results show: Soluble HIV-1, -2 and SIV Nef proteins, alone, induce apoptosis in CD4+ T lymphocytes. Nef proteins cytotoxic activity is mediated through the HIV-1 chemokine co-receptor CXCR4. The apoptotic motifs in the HIV-1 Nef protein have been localized in two 10-amino acid regions. The apoptotic region in SIV Nef protein has been localized to the C-terminal 20 amino acids. In tissue culture, Nef protein is shed into the extracellular environment. HIV-1 Nef protein has been identified in patient plasma samples, and shown to be apoptotic. A mouse model has been developed to study to study Nef-induced pathogenesis in vivo. Increased levels of apoptosis are observed in splenic lymphocytes in Nef-exposed mice. Nef and Pathogenicity.

The nef genes of Human Immunodeficiency (HIV) and Simian Immunodeficiency (SIV) Viruses encode 27-34 kd myristoylated proteins, which are expressed early after establishment of the provirus in host cells. Although largely dispensable for viral growth in cell culture, the expression of Nef results in higher viral loads and increased viral pathogenicity both in humans and in animal models for HIV/SIV infection. Correspondingly, nef-deleted SIV exhibits reduced pathogenicity, and lower viral loads when used to infect rhesus macaques. Interestingly, reversion to pathogenicity of SIVmacBK28-41 containing an attenuated nef gene was shown to be linked to the C-terminal region, which is rot found in HIV-1. Nef-deleted HIV-1 variants have been isolated from long-term survivors (LTS) of HIV-1 infection. A number of these LTS individuals remained healthy more than 10 years after a diagnosis of HIV-1 infection in the absence of ongoing antiretroviral therapy. For many of these patients, the lack of expression of Nef was the only observable attenuation of the HIV-1 virus.

Transgenic animal models have been developed to study effects of HIV expression on in vivo host systems. In these studies, lymphocyte depletion, as well as most of the organ system dysfunction found in AIDS patients was observed.

More specifically, in mice transgenic for nef, lymphocyte depletion, as well as most of the tissue specific dysfunction found in AIDS patients is observed, and the nef-transgenic mice progress to death as seen in typical cases of HIV infected individuals.

Bystander Effect—Lymphocyte Depletion.

It has been proposed that reduction and killing of lymphocytes is directly linked to the viral load, and the depletion process is induced by viral infectivity. However, Anderson et al suggested that this model for pathogenesis made too many assumptions. They suggested that if one carefully analyzes the data and makes the minimum number of assumptions, viral load/direct consequences of infection do not explain the pathogenic effects of infection. It has been proposed that lymphocyte killing leading to depletion is a result of programmed cell death. Finkel et al. reported that apoptosis predominantly occurs in uninfected or bystander cells, with a distinct lack of cell killing in the productively infected cells themselves, (bystander effect). One relevant scenario to explain lymphocyte killing leading to depletion suggests that infected cells remain viable for the production and assembly of viral particles, while the surrounding uninfected CD4+ T lymphocytes are targeted for death. A number of studies have contributed to the "bystander effect" premise that the longevity of infected cells is due to intracellularly expressed Nef protein. It has been suggested that the virus uses a strategy by which intracellular Nef protects the HIV-1-infected host cell from pro-apoptotic signals through Nef-mediated interference with the function of the apoptosis signal-regulating kinase 1 (ASK1), while simultaneously promoting the killing of bystander cells through the induction of FasL. In these studies, it was shown that ASK1, which is a serine/threonine kinase, is essential for the complete signaling of Fas and TNF-alpha death-signaling pathways. However, in the presence of Nef, a complex consisting of ASK1 and Nef is formed which prevents the normal interaction of ASK1 with the death-signaling receptors. Other researchers report a direct association of HIV-1 Nef with the zeta chain of the T cell receptor (TCR) complex and the requirement of both of these proteins for HIV-mediated up-regulation of FasL. Their data suggest that Nef can form a signaling complex with the T cell receptor (TCR) of T lymphocytes, thereby bypassing the requirement of antigen to initiate T cell activation and subsequent up-regulation of FasL expression. Long-term stable expression of Nef, which mimics persistent or latent infection in vivo, was observed to confer resistance against anti-Fas Ab-induced apoptosis through inhibition of caspase 3 and caspase 8 activation. HIV-1 Nef has also been suggested to augment HIV replication by prolonging the viability of infected cells through the blocking of p53-mediated apoptosis.

Nef and Apoptosis.

A second premise for the "bystander effect" scenario directly implicates viral proteins (i.e., Nef), or indirectly implicates virally stimulated cellular factors as mediators of bystander cell death. The N-terminal portion of the HIV-1 Nef protein has been shown to be involved in apoptosis of uninfected lymphocytes. Okada and colleagues have shown that soluble Nef protein, in conjunction with anti-Nef antibodies, is involved in the destruction of a broad spectrum of uninfected blood cells that includes CD4+ and CD8+ T-lymphocytes, B-lymphocytes, macrophages and neutrophils. This destruction leads to immune suppression. Adachi's laboratory reported that HIV-1 Nef, in concert with anti-Nef antibodies, induces apoptosis in CD4+ T lymphocytes. Specifically, Adachi's group claimed that CD4+ T cells are not killed when exposed to soluble HIV-1 Nef, but in the presence of cross-linking anti-Nef antibodies, Nef acquires cytotoxic activity against CD4+ T cells.

The bystander hypothesis hinges on the existence of soluble Nef protein in the extracellular environment. As might be expected because Nef is myristylated, it is closely associated with cellular plasmalemmas. It has been shown to (i) have multiple intracellular effects, (ii) be attached to the internal surface of the plasma membrane through the N-terminal myristylation group, and (iii) lose most of its important biological properties when the myristylation site is removed from nef by mutation. Between 60 and 200 molecules of Nef are incorporated in virions (where most are cleaved by the viral protease between residues 57 and 58 and associate with the viral core). It had been taken for granted that Nef protein does not have a significant extracellular presence. This is not correct. First, the cleaved, intravirion version of Nef could be released extracellularly through breakdown of normal or defective viral particles. Second, there is evidence that the full length Nef protein exists extracellularly in significant amounts. Full length myristylated Nef has now been shown to be released into the extracellular medium when expressed in mammalian cells in significant concentrations. Gould et al., showed that infected cells can release exosomes containing viral proteins. With the breakdown of these exosomes, the viral proteins would be released into the extracellular environment. Finally, soluble Nef protein has been detected in the sera of HIV-1 infected patients. These sera concentrations are more than enough to induce apoptosis in Jurkat cells. Thus, there is enough evidence of soluble, extracellular Nef to directly implicate Nef protein in bystander cell death leading to CD4+ T-cell depletion and AIDS.

Fujii et al, determined anti-Nef antibody titers in patient sera, and found that the anti-Nef antibody titers in these sera were inversely related to the Nef concentrations. They found that the five patient samples in which Nef was undetectable exhibited the highest titers of anti-Nef antibody. Earlier reports indicated that anti-Nef antibody levels in patient sera, both early in HIV-1 infection and after highly active antiretroviral therapy (HAART) vary significantly among individuals. Moreover, the relative strength of the anti-Nef response could be correlated with viral loads and disease progression. It was proposed that the lack of immune response to Nef may be correlated with a more rapid rate of progression to immune deficiency. Specifically, patients who developed a strong anti-Nef response at or near the time of infection were less likely to be rapid progressors to AIDS.

SUMMARY OF THE INVENTION

The invention comprises a peptide vaccine that will provide protection against Nef-mediated pathogenesis which causes T-cell depletion seen in full-blown AIDS. The identified Nef apoptotic motif peptides are attached to an immunogen such as KLH, and then injected into the subject to cause the host to generate an immune response against those epitopes, which would confer direct protection against viral protein Nef-induced pathogenesis. The vaccine is not used to induce sterilizing immunity, but to block the ability of soluble Nef protein to induce apoptosis, and to therefore alleviate lymphocyte depletion and organ damage. CXCR4-specific Nef sequences may be delivered to the mucosa or systemically. The mucosal means of application include, but are not limited to, oral, intranasal, ocular, intravaginal, rectal, and/or intraurethral administration in liquid or particulate form. Systemic means of application include parentaral administration, including intramuscular, subcutaneous and intracutaneous administration in liquid or particulate form. The active agents may be administered using targeting liposomes, microspheres, or solid supports.

DETAILED DESCRIPTION OF THE INVENTION

The body of evidence from patient, primate, transgenic animal, and cell culture studies indicate that soluble Nef protein causes pathogenic effects including T-cell depletion. In the transgenic studies, pathogenic effects due to Nef are clear, but it is not clear whether the observed pathologies are due to effects of intracellular expressed Nef, or are effects of soluble Nef protein shed by the nef-expressing cells. The in vitro work indicates that intracellular Nef protects the expressing cells, and pathogenic effects of Nef are due to extracellular, soluble Nef protein. In the transgene systems described thus far, these HIV proteins (e.g., Nef) are expressed constitutively, during embryonic development, and during early growth. It is very possible that the viral proteins will have major effects on embryonic and prepuberal growth, which would not model the effects of HIV-1 on an infected adult human. Finally, that transgene Nef protein would probably be considered 'self' by the expressing organism (mouse), and as such would not be recognized as a foreign antigen as it would in a viral infection. Thus, it is quite possible that these transgenic models have not accurately reflected the effects of Nef in HIV infected individuals.

It was found that soluble Nef protein-induced apoptosis drives some portion of HIV pathogenesis, indicating that soluble Nef protein, through the apoptotic motifs, drives CD4+ T-cell depletion. The results indicate that soluble HIV-1 Nef protein (eucaryotic or bacterially expressed) without cofactors is a potent inducer of apoptosis in a number of cell types including CD4+ T lymphocytes; (b) Nef acts through the HIV-1 chemokine co-receptor CXCR4; (c) the apoptotic motifs in the HIV-1 Nef protein have been localized in two 10-amino acid regions; (d) HIV-2 and SIV Nef also have the ability to induce apoptosis in several cell lines including T-cell lines, and this function maps to the C-terminal region of SIV.

From in vitro studies, soluble Nef protein, through the identified Nef apoptotic motif sequences, clearly interacts with a specific chemokine receptor (CXCR4) on the surface of a number of cell types including lymphocytes. Through that interaction, Nef dysfunctionally induces intracellular effects including unscheduled gene expression, and apoptosis. Thus, in vitro, soluble Nef induces effects in uninfected lymphoctyes compatible with what would be observed in a bystander cell killing and lymphocyte depletion scenario. These Nef effects would be compatible with induced pathogenesis observed in other cell systems (e.g., endothelium and vascular dysfunction). A new in vivo mouse model was developed to study Nef-induced pathogenesis. In these models increased levels of apoptosis in splenic lymphocytes in Nef-treated mice have been observed. This is a harbinger of general killing of T-cells, and can be interpreted as leading to peripheral T-cell depletion. Thus, from the body of data it was shown that soluble Nef protein is at least in part the cause of HIV/SIV T-cell depletion.

One mechanism suggested from the body of evidence discussed above, is that the Nef-induced effects in vitro and in the in vivo mouse model plays some role in T-cell depletion induced by HIV in vivo in infected patients. In this scenario, some portion of the T-cell killing leading to lymphocyte depletion is driven by soluble extracellular Nef protein through the Nef apoptotic motifs.

Nef driven T-cell depletion hinges on the existence of soluble Nef protein in the extracellular environment, and a weak immune response that does not block Nef apoptotic sequence-driven apoptosis. HIV-1 patients producing high titers of antibody directed against Nef were found to be less likely to be rapid progressors to AIDS. This shows that at the very least, one component driving T-cell depletion and AIDs is the presence of Nef protein-induced apoptosis, coupled with a weak immune response to those Nef epitopes that induce apoptosis. Out of this, one arrives at the conclusion that this process can be blocked by increasing the host immune response to the apoptosis-inducing Nef epitopes. This is accomplished through treating infected individuals with the apoptosis inducing Nef peptide in the presence of or attached to an adjuvant. Boosting of the host immune response to the apoptosis-inducing Nef epitopes results in slowing or blocking of progression to AIDS.

Materials and Methods

Proteins and Antibodies.

SDF 1a was obtained from Chemicon (Temecula, Calif.). The following antibodies were used: (1) monoclonal mouse anti human fusion clone 12G5, mIgG2a[CXCR4] (Research Diagnostics Inc., Flanders, N.J.); (3) monoclonal mouse anti human CCR5 antibody (PharMingen, San Diego, Calif.); (3) monoclonal mouse anti human CD4 antibody (American Bio Technologies, Inc., Cambridge, Mass.); (4) mouse IgG (Sigma, St. Louis, Mo.); (5) monoclonal mouse anti caspase 3 antibody (Active Motif, Carlsbad, Calif.); (6) rabbit anti HIV 1 Nef antiserum (NIH AIDS Research & Reference Reagent Program, (Rockville, Md.)); (7) Goat Anti-Mouse IgG(H+L) Label Horseradish Peroxidase (Pierce, (Rockford, Ill.)); (8) Goat Anti-Rabbit IgG(H+L) Label Horseradish Peroxidase (Pierce, (Rockford, Ill.)). Nef20mer overlapping peptide set was obtained from the AIDS Reagent Program (Rockville, Md.). Nef motif peptides were obtained from Sigma Genosys (Houston, Tex.).

Nef Expressing Plasmid.

Using PCR, the nef gene was cloned from pNL43, using a forward primer (5' GGG GGG AAG CCT CAT ATG GGT GGC AAG TGG TCA AAA AGT AGT GT 3') (Seq. ID No. 1) engineered to contain an NdeI restriction site, while retaining the start codon, and a reverse primer (5' GGA GGG CTG CAG TCA GTG ATG GTG ATG GTG ATG TCC GCC GGA TCC ACC GCA GTT CTT GAA GTA CTC CGG 3') (Seq. ID No. 2) designed to contain a linker region, followed by a hexahistidine tag, a stop codon and the PstI restriction site. The amplified sequence was ligated into the pRSETB expression vector that was previously digested using the NdeI and PstI restriction enzymes. This digestion removed the N terminal hexahistidine tag, T7 gene 10 leader and Xpress Epitope from the pRSETB vector. The recombinant plasmid, which contained a C terminal hexahistidine tag, was referred to as pRSETB Nef.

Development of the Nef Knockout Clones.

pNefΔM1. Clones expressing deletion mutant of Nef 52-61 were constructed by spliced overlap extension mutagenesis from the viral clone pNL4-3 KFS. The outer oligo primers were: 5'CCT AGA AGA ATA AGA CAG GGC (Seq. ID No. 3) and 5' GCA GTT CTT GAA GTA CTC CGG (Seq. ID No. 4). Internal PCR primers were: 5'AAT ACA GCA GCT AAC GAG GAG GAA GAG GTG (Seq. ID No. 5) and 5'CAC CTC TTC CTC CTC GTT AGC AGC TGC TGT ATT (Seq. ID No. 6).

pNefΔM1M2. Clones expressing the double knock-out were constructed by spliced overlap extension mutagenesis from clone of NefΔM1. The outer oligo primers were 5' CCT AGA AGA ATA AGA CAG GGC (Seq. ID No. 7) and 5'GCA GTT CTT GAA GTA CTC CGG (Seq. ID No. 8). The internal PCR primers were: 5'CCT GTG AGC CTG CAT GAG TGG AGG TTT GAC (Seq. ID No. 9) and 5'GTC AAA CCT CCA CTC ATG CAG GCT CAC AGG (Seq. ID No. 10).

HEK 293 cells (1×107) were transfected with 6 μg of plasmid DNA from the HIV-1 vectors described above, using Effectene transfection reagent (Qiagen) according to the manufacturer's recommendations. Cultures were then allowed to grow and express the appropriate Nef protein into the medium for 48-96 hours. The conditioned medium was then collected, analyzed for Nef protein, and used in the assays.

Expression and Purification of Recombinant HIV 1 Nef.

Full length recombinant HIV 1 Nef protein was bacterially expressed in BL21 DE3 *E coli* cells from the Nef expression plasmid pRSETB Nef. Purification of expressed recombinant HIV 1 Nef was performed using the His Bind Kit (Novagen, Madison, Wis.) in which Nef protein was affinity purified through binding of the C terminal hexahistidine tag to nickel charged tentacle methacrylate polymeric beads. Impurities were removed from the Ni bound protein by a gradient of increasing imidazole concentrations. The final product was >95% pure as judged by SDS-PAGE gel. The monomeric form of purified recombinant HIV 1 Nef protein resolved at approximately 32 kD, with a lower concentration amount of the dimeric form occurring at approximately 50 kD (Data not shown). Protein analysis using more sensitive surface enhanced laser desorption/ionization (SELDI) mass spectrometry under non denaturing conditions revealed the existence of Nef protein monomers, dimers and trimers (data not shown). This shows that the recombinant protein possessed stabilizing secondary and tertiary structures that normally exist in the native protein.

Cell Cultures.

Normal human mammary epithelial cells (Biowhittaker, Walkersville, Md.) were grown in MEGM BulletKit (Biowhittaker, Walkersville, Md.), ReagentPack (Biowhittaker, Walkersville, Md.). Normal human vascular endothelial cell (HUVEC; Biowhittaker, Walkersville, Md.) were grown in Endothelial Cell Growth Medium (EGM; Biowhittaker, Walkersville, Md.). The medium was supplemented with 10 ng/ml hEGF (human recombinant Epidermal Growth Factor), 1.0 μg/ml Hydrocortisone, 50 μg/ml Gentamicin, 50 μg/ml Amphotericin B, 12 μg/ml BBE (Bovine Brain Extract), and 2% v/v FBS (Fetal Bovine Serum).

Breast Lines. MDA-MB468 (ATCC # HTB-132), grown in Leibovitz's L-15 with 2 mM L-glutamine, 90%; Fetal Bovine Serum, 10%. MDA-MB-231 (ATCC # HTB-26), grown in RPMI 1640 medium containing fetal bovine serum 10%. MCF7 (ATCC # HTB-22), grown in minimun essential medium Eagle with 2 mM L-glutamine and Earle's BSS adjusted to contain 1.5 g/L of Sodium bicarbonate, 0.1 mM non-essential amino acids, 1.0 mM sodium pyruvate supplemented with 0.01 mg/ml bovine insulin, and containing Fetal bovine serum, 10%. DU4475 (ATCC # HTB-123) were grown in RPMI 1640 medium with 5 ml of Penicillin-Streptomycin-Glutamine, and adjusted to contain 1.5 g/L Sodium bicarbonate, 4.5 g/L Glucose, 10 mM HEPES, 1.0 mM Sodium pyruvate, with Fetal bovine serum, 10%. Media was removed, cultures rinsed with 0.25% Trypsin, 1 mM EDTA solution (GIBCO BRL, Cat # 25200072) for 5 to 10 min at RT, and spun at 2000 rpm for 15 min. The solution was removed, fresh culture medium added, and cells dispensed into fresh culture flasks. Cultures were incubated at 37° C. with 5% $CO_2$ for two to four days.

Colon Lines. SW480 (ATCC # CCL-228), grown in Leibovitz's L-15 with 2 mM L-glutamine, 90%; Fetal Bovine Serum, 10%. HT-29 (ATCC # HTB-38), grown in McCoy's 5a medium with 1.5 mM L-glutamine, and Fetal bovine serum, 10%. Prostate Lines. human prostate cell lines LNCaP (lymph node metastatic), CWR22 (primary prostatic tumor), PC-3 (lung metastatic), Du145 (brain metastatic).

Apoptosis. Terminal Deoxynucleotidyl Transferase dUTP Nick-End Labeling (TUNEL) Assay.

Apoptosis generates DNA free ends which can be labeled in situ using terminal deoxynucleotidyl-transferase (TdT), incorporating an exogenously added labeled nucleotide to the DNA strand. This label can then be visualized directly by fluorescence or indirectly using anti-FITC-peroxidase, and a calorimetric assay. Cells on coverslips were washed with PBS, and fixed for 30 minutes at RT with 4% paraformaldehyde, in PBS, pH 7.4. They were then washed with PBS, and permeabilized with 0.1% Triton X-100 for 10 minutes at room temperature (RT). The slides were rinsed twice with PBS, and air dried for 2 minutes. Then, we followed precisely the manufacturers procedure for TUNEL staining the slides (manufacturer's procedure for the In Situ Cell Death Detection Kit, AP; Boehringer Mannheim, Indianapolis, Ind.). Total cell counts were determined by counterstaining fixed cultures with 20 µg/ml of Hoechst 33258. All specimens were observed by epifluorescence on a computer-controlled microscope system based on a Zeiss Axioskop microscope (Carl Zeiss, Thornwood, N.Y.), and the images were obtained and examined using a charged coupled device (CCD) camera, MagnaFire, model S99806 (Olympus American, Melville, N.Y.). Images were examined using Image-Pro Plus 4.1 for Windows (Media Cybernetics, Silver Springs, Md.) software.

Competition Assays.

Incubated cultures ($2.5 \times 10^5$ cells/dish) for 24 to 48 hours. Cultures were then pretreated with the appropriate antibody for 30 min. at room temperature (RT). Cultures were subsequently washed with PBS, and then treated with the modulator for 24 hour. Finally, slides were stained and imaged as described above.

Immunocytochemical Assay.

Cultures were rinsed 2× with 1×PBS containing 0.1% glycine to reduce intrinsic fluorescence. They were blocked with 1% Goat serum in PBS containing 0.3% Triton X-100 at RT for 1 hr. Primary antibody (1:250) was added to the blocking solution, and the slides were incubated overnight at 4° C. The slides were rinsed 3× with 1×PBS containing 1% Triton X-100 at RT, and the second antibody (1:200) (Texas Red Anti-Mouse IgG [H+L], Vector Cat. # TI-2000, 1.5 mg/bottle) was added in the blocking solution and incubated at RT for 1 hr. The slides were then rinsed 3× with 1×PBS containing 1% Triton X-100 at RT, and fixed in 4% paraformaldehyde at RT for 60 min. Finally, they were rinsed 3× with 1×PBS, briefly dried, mounted with media-mowoil, excess oil removed and slides were visualized or stored in the refrigerator. Slides were observed by epifluorescence on a computer controlled microscope system based on a Zeiss microscope, and a CCD camera as described above. Images were subsequently examined as described above.

Cloning and Expression of HIV1, 2 and SIV Nefs.

To clone and express Nef proteins from HIV-1, HIV-2 and SIV, the nef reading frames of each virus were amplified by PCR from full length viral clones and placed into the expression vector pcDNA 3.1/V5-His TOPO (Invitrogen). The HIV-1 viral clone used was pNL4-3 (gift of Eric Freed, NIH), the HIV-2 clone was from the JK strain (HIV7312A; gift of John Kappes, University of Alabama Birmingham) and the SIV clone was from SIVmac239 (p239SpE3' nef Open; AIDS reagent program, cat # 2476). The primers used to amplify the nef reading frame from pNL4-3 were: Forward 5'-CCT AGA AGA ATA AGA CAG GGC (Seq. ID No. 11) and Reverse 5'-CAC TAC TTG AAG CAC TCA AGG C (Seq. ID No. 12). The primers used to amplify the nef reading frame from SIV p239SpE3' were: Forward 5'-CCT CTT CAG CTA CCA CCG CTT GAG AGA CTT ACT C (Seq. ID No. 13) and Reverse 5'-TGA CTA AAA TGG TCT GAG G (Seq. ID No. 14). The primers used to amplify the nef reading frame of HIV-2 were: Forward 5'-GAA GAA GGA GGT GGA AAC GAC G (Seq. ID No. 15) and Reverse 5'-AAG TGC TGG TGA GAG TCT AGC (Seq. ID No. 16). After PCR amplification each PCR product was inserted into the vector by TOPO cloning according to the manufacturer's instructions. The sequence of each clone was confirmed by dideoxy-sequencing. The functionality of each clone was verified by their ability to trans complement a nef-deleted strain of NL4-3 and restore infectivity as determined by MAGI infectivity assays.

To express Nef protein, 6 µg of each plasmid was separately transfected into HEK 293 cells using Effectene reagent (Qiagen). The Effectene was removed after 6 hours and fresh medium was added. After 48 hours the supernatants were collected and spun at 400× g to remove any cellular debris. Supernatants were either used immediately or frozen at −80° C. until use.

Apoptosis Assay: Agarose Gel Electrophoresis/DNA Fragmentation.

Untreated or treated cells were collected, and DNA was harvested from normal or cancer cell cultures. Briefly, the cells were washed with PBS, pelleted at 1600 g for 20 minutes at 4° C., and resuspended in 50 mM Tris-HCl, pH 7.5, 20 mM EDTA buffer at about $10^7$ cells/ml. The cells were then treated 2× with lysis buffer: 1.0% NP-40 (Sigma, St. Louis, Mo.) in the same Tris/EDTA buffer at RT for 2 minutes followed by centrifugation at 1600 g for 5 minutes. After the last spin, SDS was added to the supernatant to 1% final concentration, RNase A (Sigma, St. Louis, Mo.) was added to 5 mg/mil final concentration, and the solution incubated at 56° C. for 2 hours. Subsequently, protease K (Promega, Madison, Wis.) was added to the solution to 2.5 µg/ml and incubated at 37° C. for 2.5 hr. Ammonium acetate was added to 4 M final concentration, 0.7 volumes of isopropanol was added, the solution was put at −20° C. overnight followed by centrifugation at 14,000 rpm for 30 minutes. The pellets were washed twice with 70% ethanol, dried and resuspended in 10 mM Tris-HCl, pH 7.5, 1 mM EDTA. DNA samples, 18 µg per condition, were prepared in neutral loading buffer to a final concentration of 0.02% bromophenol blue, 5% glycerol, 0.1% SDS, and 50 µg of ethidium bromide, loaded onto a neutral agarose gel (1.7%), and run at 50V for 2.5 hours. DNA size standards were HindIII digested lambda DNA, and DNA ladder markers (Promega, Madison, Wis.). The resultant separated bands were visualized and photographed using a Kodak Electrophoresis Documentation and Analysis System 120 (Eastman Kodak Company, Rochester, N.Y.) with a Fotodyne transilluminator UV box.

In Vivo Nef Treatment.

Male CD-1 mice weighing 12-16 g were purchased from Charles River Laboratories. The animals were housed in the Center for Animal Resources at Morehouse School of Medicine, an approved facility, under the supervision of veterinarians and trained technicians. The mice received intraperitoneal injections with X ng/mouse of HIV-1 Nef, or buffer biweekly. Monthly, two experiment treated and one control treated mouse was sacrificed and the serum and spleen harvested. Freshly removed mice spleen were placed in 60×15-mm dishes containing 2 ml of CSC Cryopreservation freeze medium (Cell Systems, Kirkland, Wash.). Subsequently, the spleens were ground between frosted end one side of slides (Baxter Healthcare Corporation, McGaw Park, Ill.), and a pipet was used to remove cells off slides. The cell suspensions were split into two cryogenic vials (Nalge company, Rochester, N.Y.), 1 ml cell suspension/each vial, and placed at −80° C. overnight, and then moved to liquid nitrogen for long term storage.

Results.

Soluble Nef protein (HIV-1, SIV, HIV-2), both bacterially and eucaryotically expressed, without cofactors induce apoptosis in vitro in a number of cell lines including CD4+ T lymphocytes (cell lines and PBMC's).

Bacterial Expressed Nef Effects.

Jurkat or H9 cultures were exposed to soluble recombinant Nef protein at concentrations from 1 to 500 ng Nef/ml media for 24 hours, and then screened for apoptosis by TUNEL assay. Soluble Nef protein induced apoptosis in Jurkat and H9 cultures in a dose-dependent fashion, where the minimal treatment of 1 ng Nef/ml media induced 19.69%. (1.4228) and the maximal treatment of 500 ng Nef/ml media induced 54.94%. (3.3995) apoptosis, compared to 4.09%. (1.4733) apoptosis in untreated cells. Treatment with 10 ng Nef/ml media is representative of the level of soluble Nef that circulates in HIV-1-infected individuals. These findings suggest (1) exogenous Nef is capable of killing immune competent T helper cells in an apoptotic-mediated pathway; (2) the level of Nef protein present in the sera of HIV-1-infected patients is sufficient to induce apoptosis in T helper cells in virally-infected human patients; (3) the observed effects are a generalized effect to CD4+ T cell cultures.

In Vivo Nef Treatment.

Male CD-1 mice weighing 12-16 g were purchased from Charles River Laboratories. The animals were housed in the Center for Animal Resources at Morehouse School of Medicine, an approved facility, under the supervision of veterinarians and trained technicians. The mice received intraperitoneal injections with X ng/mouse of HIV-1 Nef, or buffer biweekly. Monthly, two experiment treated and one control treated mouse was sacrificed and the serum and spleen harvested. Freshly removed mice spleen were placed in 60×15-mm dishes containing 2 ml of CSC Cryopreservation freeze medium (Cell Systems, Kirkland, Wash.). Subsequently, the spleens were ground between frosted end one side of slides (Baxter Healthcare Corporation, McGaw Park, Ill.), and a pipet was used to remove cells off slides. The cell suspensions were split into two cryogenic vials (Nalge company, Rochester, N.Y.), 1 ml cell suspension/each vial, and placed at −80° C. overnight, and then moved to liquid nitrogen for long term storage.

Results.

Soluble Nef protein (HIV-1, SIV, HIV-2), both bacterially and eucaryotically expressed, without cofactors induce apoptosis in vitro in a number of cell lines including CD4+ T lymphocytes (cell lines and PBMC's).

Bacterial Expressed Nef Effects.

Jurkat or H9 cultures were exposed to soluble recombinant Nef protein at concentrations from 1 to 500 ng Nef/ml media for 24 hours, and then screened for apoptosis by TUNEL assay. Soluble Nef protein induced apoptosis in Jurkat and H9 cultures in a dose-dependent fashion, where the minimal treatment of 1 ng Nef/ml media induced 19.69%. (1.4228) and the maximal treatment of 500 ng Nef/ml media induced 54.94%. (3.3995) apoptosis, compared to 4.09%. (1.4733) apoptosis in untreated cells. Treatment with 10 ng Nef/ml media is representative of the level of soluble Nef that circulates in HIV-1-infected individuals. These findings show that (1) exogenous Nef is capable of killing immune competent T helper cells in an apoptotic-mediated pathway; (2) the level of Nef protein present in the sera of HIV-1-infected patients is sufficient to induce apoptosis in T helper cells in virally-infected human patients; (3) the observed effects indicate effect to CD4+ T cell cultures.

As was observed in the CD4+ T cell lines, soluble Nef protein induced considerable apoptosis in unstimulated human PBMCs, with similar levels to those observed in the cell lines. Unstimulated human PBMCs treated with 100 ng/ml Nef in media exhibited 41.13 (0.7939) apoptosis compared to 3.93. (0.1392) apoptosis in untreated cells. This suggests that soluble Nef is capable of killing "bystander" PBMCs in HIV-1-infected humans. Co-staining the TUNEL treated PBMC's with CD4 antibody showed that Nef-induced apoptosis was occurring in the CD4+ cell sup-population.

Nef-treated CD4+ T cells were screened for classic markers used in the identification of apoptosis. One morphological characteristic of apoptosis is nuclear fragmentation due to the actions of activated cellular proteases. Confirmation of apoptosis was provided by the detection of DNA laddering in Jurkat cell cultures exposed to soluble Nef protein. A second characteristic is activation of caspases. The active form of caspase 3 was observed after 24 hours exposure of Jurkat cell cultures to soluble Nef protein. The high molecular weight procaspase 3 (32Kd) was observed at all time points examined, with the detection of the active form of caspase 3 (17Kd) at 30 and 36 hr post treatment. Tubulin (52 Kd) was assayed as a gel-loading control. Overexposure of the filter did not result in detection of the active form of caspase 3 at or before 24 hours post treatment.

The specificity of apoptosis to Nef was shown. Nef protein was preincubated with HIV-1 Nef antiserum for 2 hours at 40° C., exposed Jurkat cell cultures to the Nef-antiserum mixture for 24 hours, and determined apoptosis by TUNEL assay. Anti-Nef antiserum reduced the number of TUNEL-labeled cells from 40.36%. (2.8419) in Nef-treated cells, to 4.43%. (1.5080), which was similar to apoptosis levels in untreated cells 1.65%. (1.3653).

Eucaryotic Cell Expressed Soluble Nef Protein Effects.

The evidence presented above clearly shows that bacterially expressed HIV-1 Nef protein is apoptotic for T-cells. However, bacterially expressed Nef protein is not the same as the final protein expressed by virally infected eucaryotic lymphocytes (e.g., the eucaryotic Nef protein would not be myristolyated). The supernatant from HIV-1, HIV-2 or SIV nef cDNA transfected 293 cells were collected, examined by Western Blot Analysis, and found to contain Nef protein. Subsequently, Jurkat cell cultures were exposed to a dilution of the Nef-containing supernatant for 24 hours under normal cell culturing conditions, and apoptosis was determined by TUNEL assay. The data clearly show that both HIV-1, HIV-2 and SIV Nef expressed by eucaryotic cells are similarly cytotoxic and apoptotic to lymphocytes.

The cell surface chemokine receptor, CXCR4, is the molecule through which Nef protein induces apoptosis in CD4+ T lymphocytes. Competition between HIV-1 Nef-induced apoptosis and (i) chemokine receptor ligands, or (ii) antibodies to these receptors showed that Nef interacted with CXCR4 to induce apoptosis. Jurkat cultures were either untreated, or pretreated with SDF-1a, or antibodies to CXCR4, CCR5, or CD4, the cultures were treated with HIV-1 Nef for 24 hours, and apoptosis was determined by TUNEL assay. Pretreatment of cultures with SDF-1a or anti-CXCR4 antibody significantly reduced the amount of Nef-induced apoptosis in these cultures. Alternatively, pretreatment with anti-CD4 antibody, or anti-CCR5 antibody had no effect on Nef-induced apoptosis.

It has been shown that the breast tumor cell line MDA-MB-468 does not express CXCR4 mRNA or protein. If Nef-induced apoptosis acts through this receptor, MDA-MB-468 line should be refractory to Nef-induced apoptosis. Alternatively, if the receptor was transfected into, and expressed in MDA-MB-468, the transfected line would then be made susceptible to Nef-induced apoptosis. MDA-MB-468 cultures were either untransfected, or transiently transfected with a CXCR4 cDNA clone, empty vector, or CCR5 cDNA clone. At 48 hours post transfection, the cultures were either assayed for cell surface expression of CXCR4 receptor by ICA, or treated with HIV-1 Nef for 24 hours and assayed for apoptosis. The transfected cultures clearly showed cell surface staining with the CXCR4 antibody, indicative of cell surface expression of the CXCR4 protein in these cells. No cell surface staining was observed with untransfected cells. Untransfected MDA-MB-468 cultures, empty vector transfected MDA-MB468 cultures, and CCR5 transfected MDA-MB-468 cultures were refractory for Nef-induced apoptosis, with background levels of apoptosis for Nef treated cultures. Alternatively, MDA-MB-468 cells expressing the CXCR4 were susceptible to Nef-induced apoptosis, displaying significant levels of TUNEL labeled cells. Thus, Nef-induced apoptosis does not occur in a cell line lacking expression of the CXCR4 receptor, but could be induced by expressing CXCR4 receptor on the surface of that cell line.

Specific physical binding to CXCR4 was assayed. The above transfection experiment (MDA-MB-468 cultures either untransfected, or transiently transfected with a CXCR4 cDNA clone, empty vector, or CCR5 cDNA clone) was assayed in the fluorescent binding assay with the Flc labeled M1 peptide. Untransfected MDA-MB-468 cells, or MDA-MB-468 cells transiently transfected with empty vector or CCR5 cDNA were refractory to binding of the Flc-M1 peptide. MDA-MB-468 cells transiently transfected with the CXCR4 clone showed significant binding of the Flc-M1 peptide. In competition analysis with MDA-MB468 cells transfected with CXCR4 clone, SDF-1a and antibody to CXCR4 blocked binding of the Flc-M1 peptide, with no blocking with a isotype control antibody. This evidence shows that Nef specifically binds to the CXCR4 receptor.

Identification of the Nef Protein Apoptotic Motif.

Nef peptides retain much of the binding and signaling activity of the full molecule. A set of 20 mer peptides with 10 aa overlaps, spanning the Nef protein (205 aa), were obtained from the AIDS Reagent Program. Jurkat cell cultures were exposed to each of the Nef peptides at 10 ng/ml for 24 hours, and screened for apoptosis. One peak of apoptosis was observed spanning peptide aa31-50 to aa7-90, peaking at aa41-60 and aa51-70. A second, smaller apoptotic peak was observed spanning peptides aa161-180 and aa171-190. Two regions of the Nef protein that induce apoptosis were identified; (1) a major apoptotic peak centering on aa50-60 (motif 1); (2) a minor peak centering on aa170-180 (motif 2). (aa sequence from HIV-1B clade NL403, Ass. No. AF070521) To determine the specificity of the apoptotic motifs, two 11 mer peptides spanning motif 1, were made, one with the correctly ordered sequence (Nef Motif 1-NAACAWLEAQ) (Seq. ID No. 17), and the other with the correct amino acids scrambled in random order (Nef scMotif 1-ALAETCQNAWA) (Seq. ID No. 18). Jurkat cell cultures were exposed to each of the two peptides at 8 ng/ml for 24 hours, and screened for apoptosis by TUNEL assay. Nef Motif 1 peptide induced 82% of the apoptosis observed using the full Nef protein. Alternatively, Nef scMotif 1 peptide induced only background levels of apoptosis observed in the untreated control. Thus, (a) Nef aa50-60 is sufficient to bind and induce an apoptotic signal; (b) induction of apoptosis is primary sequence specific. In some of the studies disclosed herein the Nef Motif 1 having an extra acid, namely TNAACAWLEAQ (Seq. ID No. 19) was administered. In this report, Seq. ID No. 17 and Seq. ID No. 19 are both referred to as M-1 or Nef Motif-1 peptide. The 11 mer sequence was easier to make than the 10 mer sequence and was found to have the same properties as the latter.

Apoptotic amino acid sequences are found in HIV-2 and in the SIV peptides which are S GLPEKEWKAR LKARGIPTE (Seq. ID No. 20) (of HIV-2) and S GLSEEEVRRR LTAR-GLLNMA DKKETR (Seq. ID No. 21) (of SIV). These would be expected to produce similar results to those found in the Nef motif-1 sequence.

Removing Nef Motifs in Full Nef Protein Eliminates Nef-Induced Apoptosis.

It would be useful to know what effect deleting the motif 1 region from the full Nef protein would have on its ability to induce apoptosis. Thus, sequences corresponding to aa 51-61 were removed from the HIV-1 cloned nef gene to produce a protein designated deltaNef. This construct was transfected into 293 cells, the cell conditioned supernatant was collected, and used in the apoptotic assay with Jurkat cells. A 5× reduction in the amount of apoptosis was observed in deltaNef treated Jurkats compared to WT Nef treated Jurkats. However, the amount of apoptosis observed in deltaNef treated Jurkats was still 3× the background levels observed in media treated Jurkats. Thus, this confirms that Motif 1 is the major apoptosis inducing region in the Nef protein. However, the residual apoptosis in deltaNef suggests that Motif 2 also plays a role in Nef apoptosis induction.

Serum from Infected Patients Displays Nef-Induced Apoptosis.

Patient serums were tested for ability to induce apoptosis in Jurkat cells. Interestingly, all serums tested displayed this ability. Subsequently, the serums with Nef antibody were treated and this experiment was then repeated. Nef antibody successfully blocked the ability of the serum to induce apoptosis, suggesting that Nef was the apoptosis-inducing serum factor. Evidence of serum Nef capable of inducing apoptosis in lymphocytes supports the general idea that soluble Nef in blood is capable of driving cell effects including cell death.

Increased Splenic Lymphocyte Apoptosis.

An in vivo mouse model was developed, in which IP injections of Nef were done over time. These mice were assayed for a number of parameters including weight, and urine collection. Mice were sacrificed at different times to assay PBMCs in serum, and the spleen for lymphocyte depletion. Observations have been made on mice treated for various time periods up to 4 months with Nef. (Members of Jolicoeurs group suggest that they observe lymphocyte depletion in Nef transgenic mice starting at about 3 months of age.) This suggests that even in juvenile mice, exposure to Nef requires 4-5 months to cause enough lymphocyte killing to begin to see lymphocyte depletion in the peripheral blood. This indicates that in adult mice, lymphocyte killing leading to peripheral blood lymphocyte depletion will require an extended period of time (>2 months). However, increased levels of apoptotic lymphocyte should be observed early (<2 months), particularly in the spleen. Splenic lymphocytes have been harvested and assayed for apoptotic cells by TUNEL and caspase 3 assay. At two months into the treatment regimen, increased levels of apoptotic lymphocytes were observed in the spleen of Nef treated mice compared to buffer treated mice. This clearly indicates that CD4+ lymphocytes are dying.

Studies of Mouse Thymus.

Nef motif 1 was administered to mice for one month by ip injection with either Nef motif 1 (Seq. ID No. 19), the 11 mer sequence or the scrambled apoptotic sequence Seq. ID No. 18. Significant apoptosis was observed in the thymus of mice treated for one month with the Nef motif 1. No apoptosis was observed in the thymus of the mice treated for one month with the scrambled peptide. This provides further indication of the ability of the Nef protein to inhibit immune response related to CD4+ peripheral blood lymphocytes.

Effect of KLH-M1 Pre-Immunization on CD4+ Cell Counts and Apoptosis.

Nef Motif 1 peptides linked to keyhole limpet hemagluttinin (KLH) were administered to 9 mice. Subsequently, the pre-immunized mice and the naive mice were either unchallenged or challenged with Nef peptide for a month. The mice were sacrificed and the PBLs collected. It was found that the administration of the Nef apoptotic peptide alone induced peripheral lymphocyte depletion and did not stimulate a resultant protective humoral response. Alternatively, pre-immunization with the Nef apoptotic peptide linked to an immune enhancing peptide gave rise to protective humoral response against the Nef epitope. Hence, it was found that the immune response protected the mice who had been administered Nef Motif from Nef apoptotic motif-induced peripheral lymphocyte depletion.

The results above show that treatment with the Nef apoptotic peptide alone may not prevent peripheral lymphocyte depletion or stimulate sufficient protective humoral response to provide appreciable protection. However, pre-immunization with the Nef apoptotic peptide motif linked to an immunogen raises a protective humoral response against that epitope. This response protects the organism from the Nef apoptotic motif-induced peripheral lymphocyte depletion.

The adjuvant/immune enhancer used with the peptides of the invention will depend on the practice within the country of intended use. While keyhole limpet hemagluttinin was the immunizing moiety exemplified the peptides of the invention may be fused to other peptides that act as adjuvants to increase antigenicity. Such fusion proteins may be produced by recombinant technology using plasmids containing hybrid genes for expression of the desired fusion proteins. Any of the compositions may contain, addition-ally, adjuvants such as alum or Freund's adjuvant.

The administration of the Nef Motif 1 peptides with at least one adjuvant presents several advantages. First of all, the peptides will not mask the antibodies to the HIV infection itself, since Nef peptides are not the peptides used to test for antibodies to HIV. A patient who may be exposed to HIV infection such as a rape victim or a care giver can be protected from detriment to the immune response during a period when it is not clear if infection has taken place without rendering them HIV positive.

A second benefit of the instant invention is that the administration of the immunogenic peptide/adjuvant combination can provide protection to the presently infected HIV patient from the nefarious effects of circulating Nef arising on account of the infection.

Larger peptides containing the Nef Motif peptide may by used to provide the benefits described herein. However, the 10 amino acids of Seq. ID No. 18 must be present in the sequence administered. The peptides of the invention may be prepared as solutions in pharmaceutically acceptable carrier such as saline, 10% dextrose, lactose in saline. Such solutions may be administered parenterally or in droplet form or sprays. The peptides bound to the antigenic molecules may also be lyophilized and administered to the mucous membranes in powder form. Peptides may be prepared in liposomes by usual method known in the art. Drops may be administered intranasally or sublingally. Sprays are particularly useful for nasal administration.

What is claimed is:

1. A method of generating a immoral immune response against a human immunodeficiency virus type 1 (HIV-1) Nef protein apoptotic motif in a subject comprising administering to the subject an effective amount of a Nef apoptotic motif peptide consisting of an amino acid sequence selected from the group consisting of SEQ ID NO: 17 (NAACAWLEAQ) and SEQ ID NO: 19 (TNAACAWLEAQ), wherein said Nef apoptotic motif peptide is linked to an immunogen.

2. The method of claim 1, wherein the effective amount of a Nef peptide linked to an immunogen is in a pharmaceutically acceptable carrier.

3. The method of claim 1, wherein the immunogen is keyhole limpet hemocyanin.

4. The method of claim 1, wherein the effective amount of a Nef peptide linked to an immunogen is administered using targeting liposomes, micro spheres, or solid supports.

5. The method of claim 1, wherein the effective amount of a Nef peptide linked to an immunogen is administered in a liquid form.

6. The method of claim 1, wherein the effective amount of a Nef peptide linked to an immunogen is administered in a particulate form.

7. The method of claim 1, wherein the effective amount of a Nef peptide linked to an immunogen is administered by mucosal administration.

8. The method of claim 7, wherein the mucosal administration is oral, intranasal, ocular, vaginal, rectal or intraurethral administration.

9. The method of claim 1, wherein the effective amount of a Nef peptide is administered by systemic administration.

10. The method of claim 9, wherein the systemic administration is parenteral, intramuscular, subcutaneous, or intracutaneous administration.

* * * * *